US007304453B2

United States Patent
Eaves (10) Patent No.: US 7,304,453 B2
(45) Date of Patent: Dec. 4, 2007

(54) METHODS AND SYSTEMS FOR ASSEMBLING BATTERIES

(75) Inventor: Stephen S. Eaves, Charlestown, RI (US)

(73) Assignee: Modular Energy Devices, Inc., Warwick, RI (US)

( * ) Notice: Subject to any disclaimer, the term of this patent is extended or adjusted under 35 U.S.C. 154(b) by 0 days.

(21) Appl. No.: 11/200,242

(22) Filed: Aug. 10, 2005

(65) Prior Publication Data

US 2006/0076923 A1    Apr. 13, 2006

Related U.S. Application Data

(60) Provisional application No. 60/601,253, filed on Aug. 13, 2004.

(51) Int. Cl.
*H02J 7/00* (2006.01)
(52) U.S. Cl. ........................ 320/120; 320/107
(58) Field of Classification Search ............ 320/120, 320/126, 107; 307/37
See application file for complete search history.

(56) References Cited

U.S. PATENT DOCUMENTS

| 3,778,634 | A | 12/1973 | Hanrihan |
|---|---|---|---|
| 4,061,955 | A | 12/1977 | Thomas |
| 4,143,283 | A | 3/1979 | Graf |
| 4,287,267 | A | 9/1981 | Whittlesey |
| 4,672,228 | A | 6/1987 | Swoboda |
| 4,673,826 | A | 6/1987 | Masson |
| 4,694,194 | A | 9/1987 | Hansel |
| 4,709,202 | A | 11/1987 | Koenck |
| 4,760,322 | A | 7/1988 | Crampton |
| 4,871,956 | A | 10/1989 | Barrella |
| 4,876,495 | A | 10/1989 | Palanisamy |
| 5,034,290 | A | * 7/1991 | Sands et al. ............. 429/120 |
| 5,103,156 | A | 4/1992 | Jones |
| 5,151,644 | A | 9/1992 | Pearson |
| 5,153,496 | A | 10/1992 | LaForge |
| 5,168,206 | A | 12/1992 | Jones |
| 5,206,578 | A | 4/1993 | Nor |
| 5,218,284 | A | 6/1993 | Burns et al. |

(Continued)

FOREIGN PATENT DOCUMENTS

EP    0932240    7/1999

(Continued)

*Primary Examiner*—Bao Q. Vu
*Assistant Examiner*—Aaron Piggush
(74) *Attorney, Agent, or Firm*—Michael de Angeli (57) ABSTRACT

A large battery pack of specified voltage and capacity can be assembled from a plurality of identical small cells by dividing the specified capacity by a nominal battery module capacity to determine a desired number of parallel modules to be provided, dividing the nominal battery module capacity by a nominal cell card capacity, to determine the number of cell cards required in each module, connecting the call cards in parallel to a common buswork to form the battery module, and connecting the modules in parallel to obtain the specified battery pack capacity and in series to obtain the specified battery pack voltage Protection circuitry can be implemented at the module level, by disconnecting one or more modules or the entire battery pack if a fault at the module level is identified; at the cell card level, by disconnecting a cell card if a cell within it is determined to be faulty; and/or internally, in each cell.

4 Claims, 6 Drawing Sheets

U.S. PATENT DOCUMENTS

| | | |
|---|---|---|
| 5,243,269 A | 9/1993 | Katayama |
| 5,313,152 A | 5/1994 | Wozniak |
| 5,422,558 A | 6/1995 | Stewart |
| 5,498,950 A | 3/1996 | Ouwerkerk |
| 5,504,415 A | 4/1996 | Podrazhansky et al. |
| 5,539,297 A | 7/1996 | Fiebig |
| 5,898,291 A * | 4/1999 | Hall ............................ 320/121 |
| 5,948,556 A * | 9/1999 | Hall et al. ...................... 429/7 |
| 5,952,815 A | 9/1999 | Rouillard |
| 6,100,804 A * | 8/2000 | Brady et al. .............. 340/572.7 |
| 6,152,776 A | 11/2000 | Ikeda et al. |
| 6,420,852 B1 | 7/2002 | Sato |
| 6,451,463 B1 * | 9/2002 | Tsai et al. ....................... 429/9 |
| 6,819,081 B2 * | 11/2004 | Izawa et al. ................. 320/107 |
| 6,919,707 B2 * | 7/2005 | Kawai et al. ................ 320/117 |

FOREIGN PATENT DOCUMENTS

EP  1150132  4/2001

* cited by examiner

FIG. 8 (BATTERY MODULE)

FIG. 9

METHODS AND SYSTEMS FOR ASSEMBLING BATTERIES

CROSS-REFERENCE TO RELATED APPLICATIONS

This application claims priority from Provisional Application Ser. No. 60/601,253, filed Aug. 13, 2004.

BACKGROUND OF THE INVENTION

The disclosed methods and systems relate generally to a method of assembly of large battery packs from battery cells, and more specifically to assembly of high-energy battery packs from series-parallel arrays of small battery cells.

Applications of rechargeable batteries often require large battery packs having high voltages and high capacities. For example, battery packs used for power backup in telecommunications outdoor installations typically require 48 volts (V) and capacities of 50-1000 ampere-hours (Ah) to yield 0.25-5 kilo-Watt (kW) power outputs. Similarly, a battery pack capable of powering an electric automobile is typically required to have a voltage of 150-300 V and a capacity of 100-200 Ah to yield power outputs of 50-100 kW. Batteries capable of storing comparable amounts of energy are referred to herein as "large batteries". Lead-acid and nickel-cadmium batteries are commonly used for these applications, and the battery packs are constructed by connecting a requisite number of large battery cells in series to satisfy the voltage requirements of the applications. Because these conventional batteries are based on an aqueous (i.e., water-based) electrolyte, they are considered safe systems, and large battery cells with tens to hundreds of ampere-hours capacity per cell can be built and used safely to assemble high energy battery packs of the type mentioned above. It is also known that because of their aqueous electrochemistry involving electrochemical reactions capable of equalizing the capacities of individual cells in a series string, the construction of large, high-voltage battery packs from aqueous battery cells does not require sophisticated battery management electronics (BME) to balance the capacities of individual cells in the string. Thus, construction of high-energy battery packs from large aqueous battery cells is a relatively simple process.

A practical disadvantage of aqueous batteries is their low energy densities, amounting to 70-200 Wh/liter, and low specific energies of the order of 30-70 Wh/kg, at the cell level. Many modern applications that call for very high power outputs and long operational times require batteries with significantly higher energy densities and specific energies. In this respect, Lithium-ion ("Li-ion") batteries are an excellent choice by virtue of their very high specific energy of 180-200 Wh/kg and energy density of 450-500 Wh/liter at the cell level; however, large Li-ion battery packs have not yet been fully commercialized because of safety concerns and the cost of large battery cells.

The Lithium-ion battery is presently the power source of choice for portable consumer products the power requirements of which can be met by small battery packs, such as cellular telephones, personal digital assistants, video cameras, and notebook computers. These sample applications are filled by small commercial Li-ion cells, such as the industry standard "18650" cell type. In typical portable applications, small battery packs are constructed from several of these 18650 cells by connecting them in series and parallel as needed to meet the voltage and capacity requirements.

There are significant differences in the electrochemistries of conventional aqueous batteries and of Li-ion batteries that impact the construction of large battery packs from Li-ion cells. The electrochemistry of the non-aqueous electrolyte used in the Li-ion battery involves reactions that do not permit series/parallel stacking of cells to form batteries without electrolyte decomposition during charge and discharge cycling of such batteries, that is, unlike the aqueous battery systems, which are much more tolerant of over- and under-charging. Consequently, battery management electronics (BME) are needed to prevent overcharge and over-discharge of the Li-ion cells, in order to avoid electrolyte decomposition and failure of battery cells under these conditions. BME are also needed to balance the capacities of the individual cells in the battery pack during cycling. Accordingly, the assembly of battery packs from Li-ion battery cells require the use of sophisticated BME.

In the case of small battery packs used in cellular telephones and computers, the BME are relatively simple because the battery pack requires only one or two small cells stacked in parallel, or a few cells stacked in series and parallel. For example, a typical battery pack for a notebook computer has a voltage of 14.4 V and a capacity of 4 Ah, and is constructed from two parallel-connected strings, each of four 18650 size Li-ion cells stacked in series. Similarly, Li-ion battery packs used for powering cellular phones commonly have a nominal capacity of about one Ah and a nominal voltage of 3.6 V and can be constructed from a single Li-ion cell. In general, the BME required for Li-ion battery packs constructed from a few cells are of low complexity, irrespective of the size of the battery cells, and the complexity of the BME increases as the number of cells in the series/parallel assembly in the battery pack increases.

Thus, while the advantages of Li-ion batteries in terms of high power density are well-known, and while Li-ion batteries are well-accepted for small battery pack use, the art has not provided a suitable Li-ion battery construction that is suitable for fabrication of large batteries.

SUMMARY OF THE INVENTION

The present invention relates to a simple, efficient, and scalable structure for a large battery assembled of series/parallel connected Li-ion cells. In one aspect of the invention, a number of individual cells are arranged onto "cell cards". The cell cards are connected in parallel by common buswork to make battery "modules". Each cell card, and each module, preferably incorporate separate Battery Management Electronics ("BME"). A complete "battery" may comprise a single module, or multiple battery modules can be connected in series and/or parallel to make up a larger "battery pack". This arrangement has numerous advantages, discussed further below.

BRIEF DESCRIPTION OF THE DRAWINGS

The invention will be better understood if reference is made to the accompanying drawings, in which.

DESCRIPTION OF THE PREFERRED EMBODIMENTS

To provide an overall understanding of the invention, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail, and therefore, unless otherwise specified, it is to be understood that features, components, and/or aspects of the illustrations can be otherwise combined, separated, interchanged, and/or rearranged without departing from the disclosed systems or methods. Additionally, the shapes and sizes of components are also exemplary and unless otherwise specified can be altered without affecting the scope of the disclosed and exemplary systems or methods of the present disclosure.

The methods of assembling a battery from a number of small cells and the batteries themselves disclosed in detail herein are directed toward large batteries storing several hundred to thousands of Watt-hours of energy in a series/parallel arrangement of small cells, which can be Li-ion cells. The disclosed methods and systems provide for an integrated approach that reduces internal wiring, increases energy density, suppresses the spread of fire, and provides an integrated electrical/mechanical design. The methods and systems thus relate to manufacturing high energy Li-ion batteries from a large number of small Li-ion cells using sophisticated BME, which is desirable because such small 18650 size Li-ion cells are safe and available at low cost.

More specifically, due to safety hazards of high energy Li-ion batteries fabricated from large battery cells, e.g., cells each having 50-200 Ah capacity, large Li-ion batteries have not yet successfully penetrated the market dominated by lead-acid batteries for applications such as electric vehicles and telecommunications back-up power systems. These safety concerns relate to the flammable electrolyte used in Li-ion cells, which can ignite due to an internal short circuit or accidental overcharge coupled with thermal runaway reactions. Small cell producers have overcome these limitations with internal thermal switches in the cells that permanently disconnect the cell from the battery during these abusive conditions. More specifically, the safety hazard associated with a battery cell is roughly proportional to the amount of stored energy in the cell. Because of an inability to quickly dissipate internal heat caused by failure, large Li-ion cells have not been able to utilize the safety protection techniques applicable to small cells. Consequently, the use of large Li-ion cells having capacities of the order of 50-200 Ah has not been considered a safe alternative for large battery applications.

A number of high volume manufacturers manufacture small safe cells in standard sizes. A typical 18650 Lithium-ion cell has a nominal voltage of 3.7V and a nominal capacity of 2.4 Ah. The 18650 cell format is also available for the Nickel metal-hydride chemistry. It is estimated that over 800 million Lithium-ion cells are made annually in the 18650 cell format. High volume, automated manufacturing, and competition help to maintain these cells at competitive prices and high quality. Because a limited amount of energy is stored in these cells, they are considered safe. Large batteries constructed from the appropriate series-parallel stacking of large numbers of these cells can provide a safe method of construction.

It has been generally believed that parallel operation of a large number of small battery cells is undesirable since the cells may not share the total battery current evenly, thereby increasing the possibility of overheating and damaging individual cells. For example, a short circuit in one cell could be supplied by other cells that are connected in parallel with it, causing catastrophic failure. It has also been generally believed in the industry that increasing the number of cells in the pack will be detrimental to pack reliability because of an increase in overall parts count.

One prior art system disclosed by Hall et. al. in U.S. Pat. No. 5,948,556 describes a massively parallel battery module for spacecraft wherein many small battery cells are connected in parallel, where each cell has over-current and over-temperature protection. A disadvantage of this system is the inability of the architecture to tolerate a cell with a high resistance internal short circuit, sometimes referred to as a "soft" short. In this type of failure, a cell loses its ability to maintain charge during extended standing periods. If connected to other cells in a parallel arrangement, the cell with the soft short not only dissipates its own charge, but also the charges of the cells in parallel with the soft-shorted cell. The current flow due to the soft short may not be large enough to activate the over-current mechanisms described in the prior art system, nor does such soft short condition produce enough heat to activate an over-temperature mechanism.

Another possible failure mode in prior art systems is that a short circuit current may activate the small Li-ion cell's internal thermal switch, usually a polymeric Positive Temperature Coefficient (PTC) circuit protection device, but not the series fuse. The PTC is a common component in lithium-ion cells that draws a small amount of heating current while the short is present, thus draining the cells of their energy while the battery is in an idle state. Thus, in prior art systems, the occurrence of a soft short will completely disable the battery pack over an extended time.

In commonly-assigned U.S. patent application Ser. No. 10/361,110, incorporated herein by reference in its entirety, a electronic architecture is presented to construct large battery packs from small commercial Li-ion cells arranged as battery modules, thereby overcoming the deficiencies of the prior art. According to this electronic architecture, a high energy battery pack is constructed using a large number of relatively small battery cells such as the 18650 size Li-ion cells. The design is modular, enabling the efficient assembly of high energy battery packs from a relatively large number of small Li-ion cells. The battery pack includes a number of series and parallel connected battery modules, and each module has a number of parallel connected cell cards. Each cell card contains a series-parallel arrangement of battery cells and associated thermal and electrical protection devices. The cells and circuitry are mounted to a printed circuit board. The cells within the cell cards are monitored for indications of failure by a protection circuit. The protection circuit will electrically disconnect the damaged cell card from the module's internal power bus when the failure criteria is met. The architecture allows a limited number of cell failures within the pack, including a "soft short" in one or more cells, without severe loss in overall battery performance. That is, the cell cards and modules are designed with respect to a given desired overall battery capacity so as to contain enough cell cards that the battery loses only a fraction of its overall capabilities when a cell card is disconnected from the module power bus. While the methods and systems disclosed in Ser. No. 10/361,110 thus relate to an electronic architecture allowing manufacture of high energy Li-ion cells from a large number of small cells, the methods and systems disclosed herein relate to the corresponding mechanical design and assembly method for battery modules and packs using commercial cells such as, for example, the 18650 size Li-ion cells.

Figure 1:
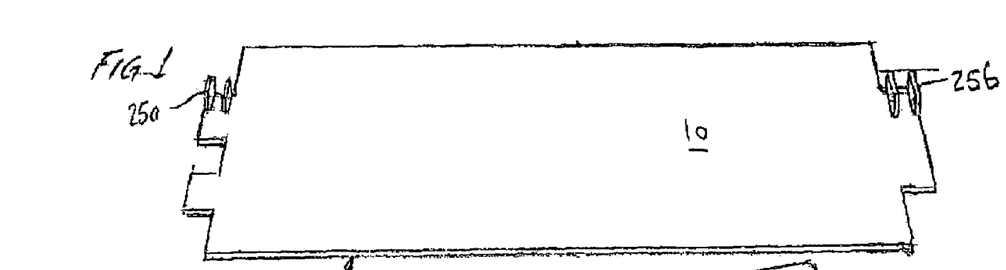
FIG. 1 is a schematic view of a cell card, showing the physical disposition of the battery management electronics and other components, before the cells are installed.
Figures 2, 10:
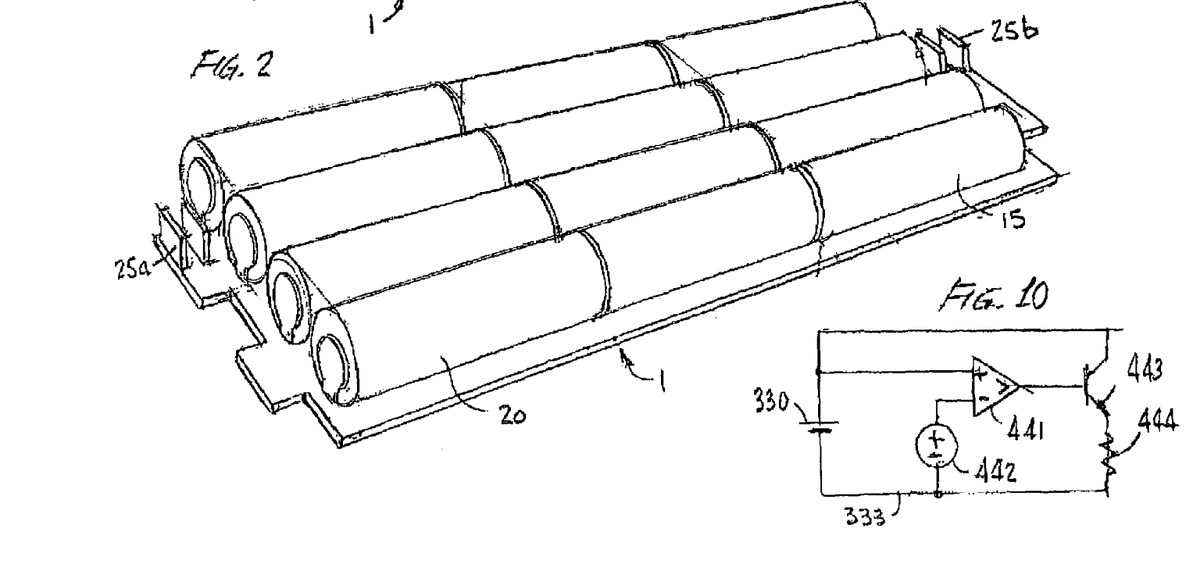
FIG. 2 is a perspective view of a cell card with cells installed.
FIG. 10 is a schematic diagram of a cell equalizer circuit.

In one embodiment, a battery module is constructed of a number of essentially identical "cell cards" 1 fitted with the individual battery cells. Referring to FIG. 1, the "bare" cell card comprises a printed circuit board 10 having assembled to it battery management electronics (BME) that include an integrated circuit(s) 5, the functions and circuitry of which are discussed below. Terminals 25a and 25b are also assembled to board 10. As shown by FIG. 2, the cell card 1 is completed by assembly thereto of a plurality of small cells 15, physically positioned on board 10 adjacent to the battery management electronics 5, and occupying an area of space no larger than the board perimeter. The cells 15 can be connected in series and in parallel (as discussed in detail below), forming a cell card 1. The number of cells 15 in series on the cell card 1 determines the nominal cell card voltage VBC, while the number of cells 15 in parallel determines the nominal cell card capacity CBC. Such a configuration provides a cell card 1 with a nominal stored energy of VBC×CBC. In the illustrated embodiment, and as discussed below in connection with FIG. 4, where cylindrical cells are used, a portion or more of the cell card electronics/BME 5 may reside in a space 20 created at the longitudinal intersection of adjacent cells by the cylindrical shape of the cells 15.

With continued reference to FIG. 2, electrical terminals 25a, 25b, to which the cells are connected, provide the positive and negative outputs of the cell card 1. Thus, the cell card 1 represents an integrated electronic/mechanical component that can reduce the requirement for discrete wiring between the cells and electronics. The resulting cell card 1 is compatible with automated manufacturing techniques using standard electronics assembly equipment, thus reducing overall manufacturing cost and increasing quality.

Figure 3:
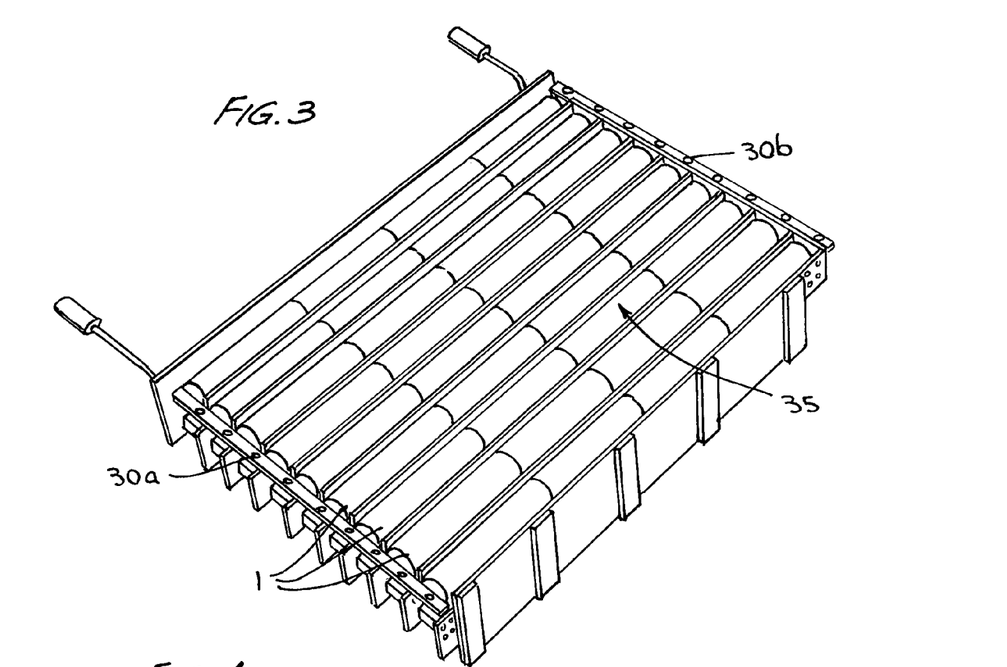
FIG. 3 is a perspective view of a large battery module, with its enclosure removed, constructed from nine cell cards connected to common negative and positive power buses.

Referring to FIG. 3, in one embodiment of a large battery module, nine substantially identical cell cards 1, as in FIG. 2, can be arranged in tandem, aligned parallel to one another and connected by positive and negative bus bars 30a and 30b. The cell cards 1 are arranged in the same orientation and make substantially rigid attachment to bus bars 30a, 30b at each end, forming a battery cell "stack" 35. Bus bars 30a, 30b are oriented orthogonal to the axial direction of the cards, and are connected physically to the terminals 25a and 25b on each cell card, mechanically connecting the cards and strengthening the assembly while providing parallel connection of the cell cards. Accordingly, the bus bars 30a and 30b have both mechanical and electrical functions, thereby reducing the weight and volume of the battery module. A battery may comprise a single module, as shown in FIG. 3, or may be made up of plural modules, connected in series and/or parallel as may be desirable, as discussed below in connection with FIG. 7.

Figure 4:
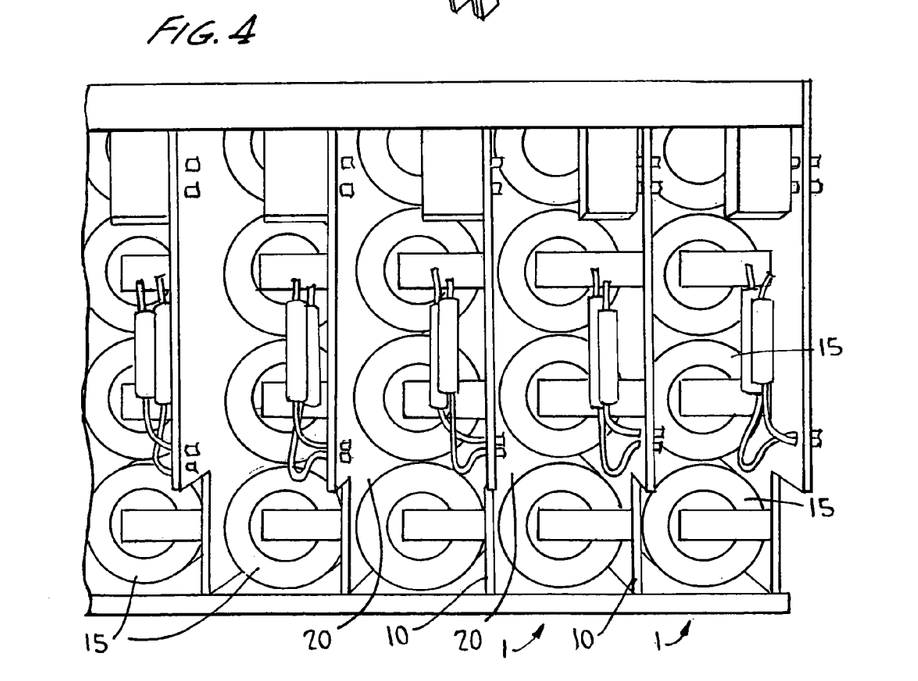
FIG. 4 is a side view of a battery module sub-assembly illustrating the arrangement of cell cards, each comprising a printed circuit board, a number of cells, and associated electronic components.

An additional feature of the disclosed methods and structure is that each layer of cells in the assembly is separated by the fire resistant printed circuit board material of which the cell cards are fabricated. This is exemplified in FIG. 4, showing an end view of the cell cards 1, each comprising a circuit board 10 with cells 15 assembled thereto. If a cell is on fire, for example, the circuit board 10 can prevent the spread of such fire to adjacent cell cards 1. Further, the use of cell cards 1 to construct battery modules through common terminal buses allow the capacity of the module to be varied by varying the number of cell cards 1 used to construct the module. Accordingly, the same cell card can be used to construct battery modules having a variety of capacities as required by different applications, reducing tooling costs and the like. Similarly, the voltage of the battery module can be conveniently varied by using cell cards of varying voltages.

Figure 5:
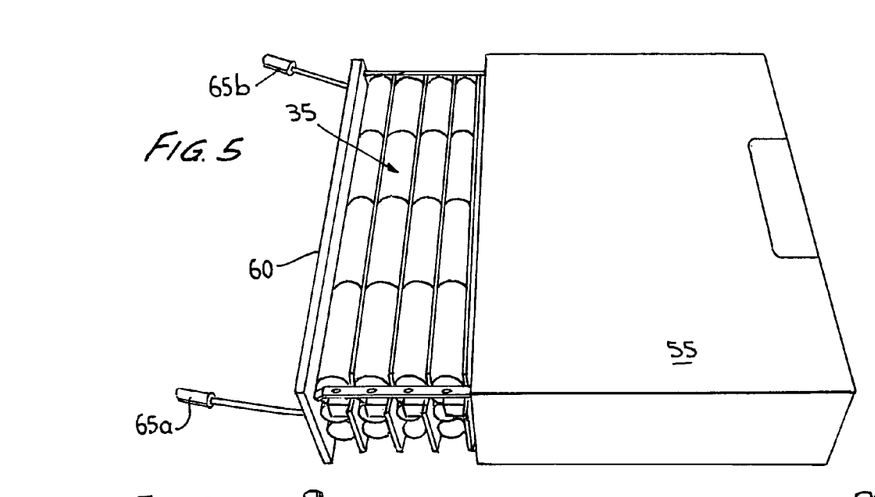
FIG. 5 displays the manner of assembly of a large battery module, as in FIG. 3, into a battery module enclosure.

FIG. 5 shows a completed battery module subassembly or "stack" 35 being inserted into an enclosure 55, having been fitted with enclosure front cover 60. Battery module connectors 65a, 65b are connected to the internal buses 30a, 30b, respectively, shown in FIG. 3. The total capacity of the resulting battery module is given by the sum of the capacities of the cell cards CBC, and the voltage VBC of a single cell card 1 gives the voltage of the module. Accordingly, for a battery module constructed from N cell cards, the total capacity is N·CBC and the voltage is VBC (assuming the cell cards are connected in parallel) to yield a nominal stored energy of N·CBC·VBC; a battery made up of Z modules would have a total capacity of Z·N·CBC·VBC.

Figure 6:
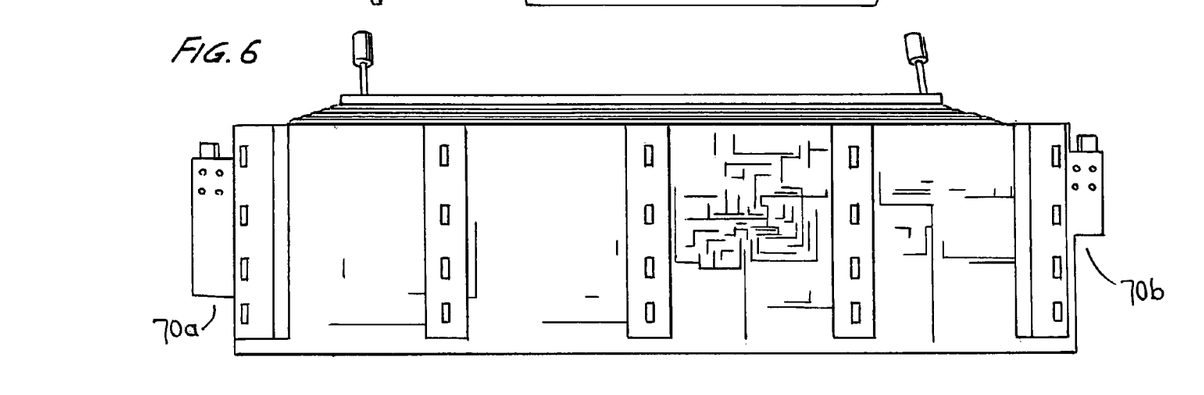
FIG. 6 is a back view of a battery cell card stack showing ventilation channels.

FIG. 6 is a back view of stack 35, illustrating an optional design for improved cooling and/or heating of the battery module. Cooling channels 70a, 70b in each cell card 1 allow for entry and/or exit of (e.g., conditioned) air and/or a cooling fluid, for example. In one embodiment, air can be circulated into a first cooling channel 70a, travel from left to right through the spacings 20 created by the curvature at the intersections of the cylindrical cells (as illustrated by FIG. 4), and exit from a second cooling channel 70b. Electronic components, as required to form the various series and parallel connections of the cells, and to provide Battery Management Electronics ("BME"), can also be located in such spacings 20.

Provided herein, for example only, is one embodiment of connecting such cells, although it will be understood that other embodiments can be used. As described in co-pending U.S. patent application Ser. No. 10/361,110, and with reference to FIG. 7, a plurality or "stack" of battery modules 101a-n, such as the battery modules described herein relative to FIGS. 1-6, are connected in series to create a battery "pack", typically having a voltage equal to the sum of the voltages of each the battery modules 101a-n, although the modules could be connected in parallel, or a combination of series and parallel, as needed to obtain any desired voltage for the overall battery.

As noted above, an important aspect of the invention is the provision of effective protection of the overall battery from problems caused by a fault in one or more cells of a given cell card. The "cell cards" described herein, for this purpose, are the same as the "energy storage sections" disclosed in the pending application Ser. No. 10/361,110. As such, a cell card or an energy storage section is defined by the existence of a non-resettable disconnect device, operable upon detection of a failure somewhere on that cell card, that isolates the cell card from the rest of the module.

Figure 7:
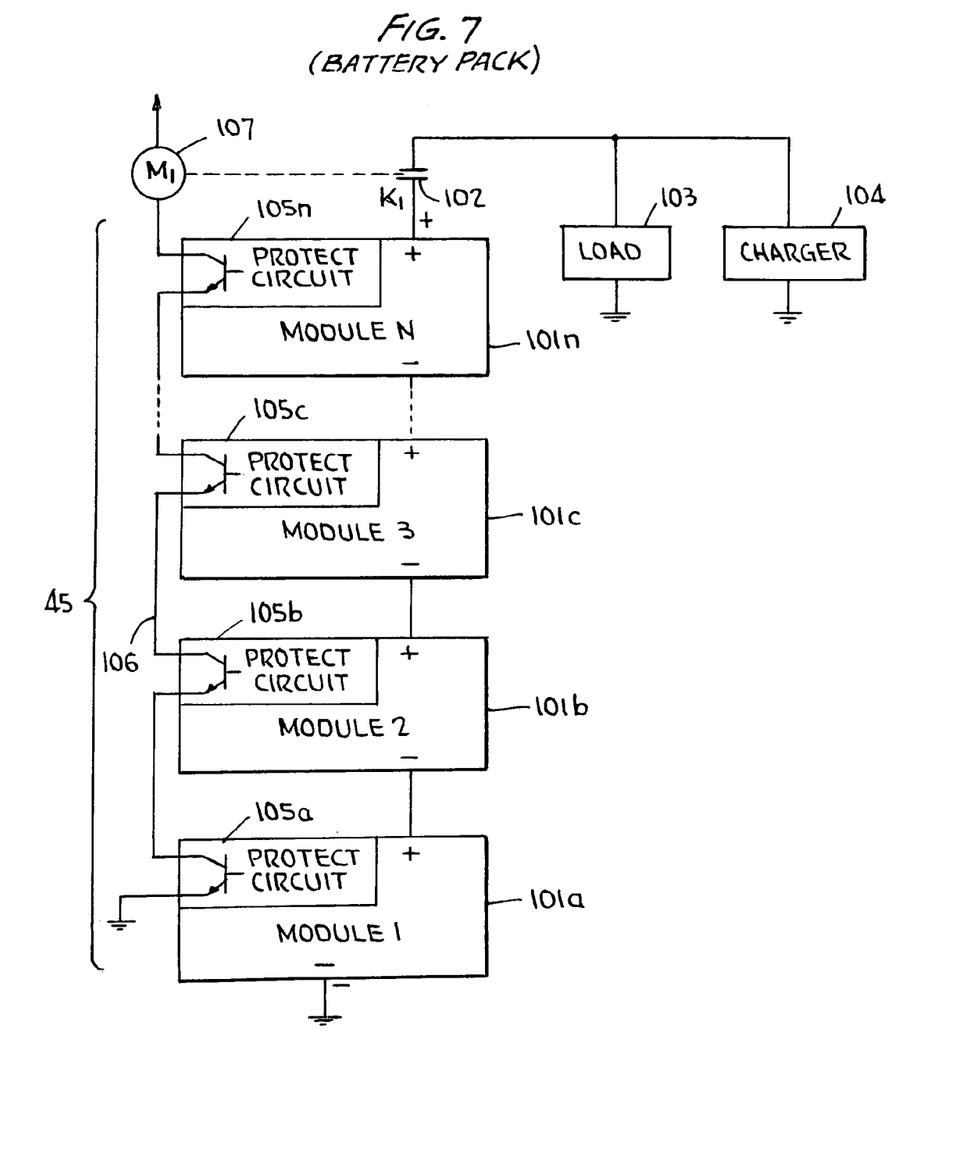
FIG. 7 is a block diagram of the circuitry of an exemplary battery, assembled from a number of battery modules.

As shown in FIG. 7, protection is preferably also provided at the module level. More specifically, a pack disconnect device 102, e.g., a relay, can be connected in series with the modules 101a-n making up the battery pack 45, and can be operated to interrupt the connection of the battery pack to a load 103 and/or charge source 104. The pack disconnect device 102 can be opened and/or otherwise activated by battery module protection circuitry 105a-n typically provided in each of the battery modules 101a-n, each module protection circuit 105a-n being capable of determining whether the corresponding battery module 101a-n is operating properly. The connection between the modules 101a-n and the disconnect device 102 may be analog, digital, or a combination, and can include software, and the disconnect device 102 accordingly may be analog and/or digital. For example, each battery module protection circuit 105a-n may be arranged to alter the continuity of an interlock signal carried by a conductor 106 connected in series between battery modules 101a-d, responsive to operation of the corresponding module 101a-n. In this case, when a battery module protection circuit 105a-n interrupts the continuity of the interlock signal, a disconnect device actuation circuit 107 can be activated, so that the illustrated pack disconnect device 102 disconnects the battery pack from the load 103 and/or charge source 104.

Those of ordinary skill will understand that the disclosed methods and systems are not limited to four battery modules as provided in FIG. 7, that is, that use of the variable N in FIG. 7, and in other Figures, represents an integer number greater than zero. Similarly, the disconnect device actuation circuit 107 can be analog and/or digital, and although the illustrated system indicates a separate module protection circuit 105a-n for the battery modules 101a-n, in some embodiments, a single module protection circuit 105a-n may receive data from multiple battery modules 101a-n. It can be understood that references herein to module protection "circuitry" 105a-n can be understood to refer similarly to a module protection "device" that can include analog and/or digital hardware and/or software.

With reference to embodiments such as those presented in FIGS. 1-4 herein, the aforementioned module protection circuits 105a-n can include BME which can be located on the circuit cards 10 and can, in some embodiments, be located in a spacing created at a longitudinal intersection of cylindrical cells, for example.

Figure 8:
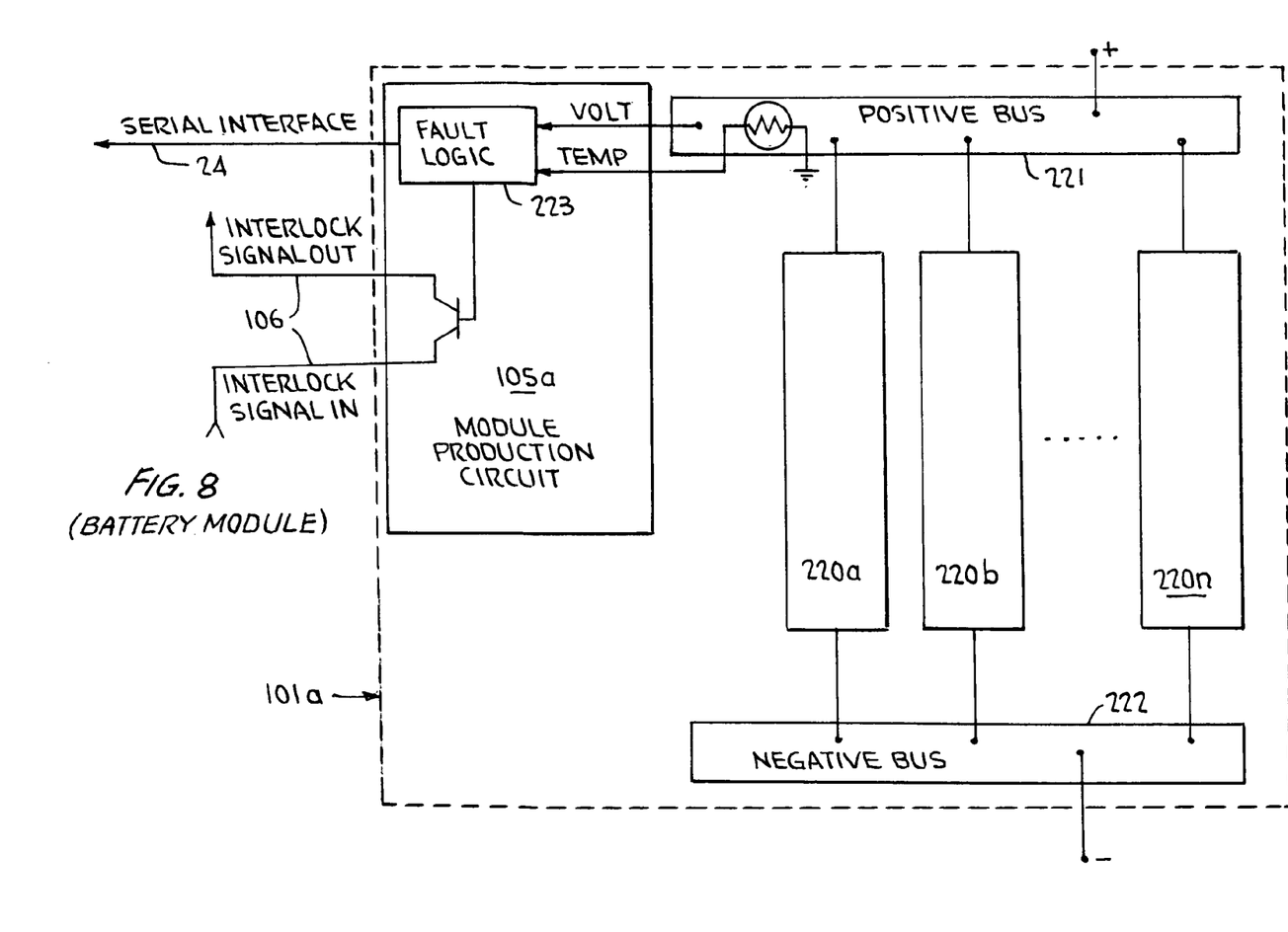
FIG. 8 is a block diagram of an exemplary battery module, made up of a number of cell cards as above.

FIG. 8 illustrates one of the battery modules 101a according to FIG. 7, where the illustrated modules include one or more cell cards 220a-n connected in parallel between positive and negative power buses 221, 222. As will be provided herein, conditions on the positive power bus 221 can be monitored by a module protection circuit 105a-n according to FIGS. 7 and 8. The illustrated module protection circuit 105a includes fault detection logic 223 that interrupts the continuity of the interlock signal 106 if a module parameter is determined to be outside of predetermined suitable operating ranges. As indicated in FIG. 8, the fault detection logic 223 can receive data and/or measure parameters responsive to conditions on the cell cards 220a-n. Such data can include, for example, voltage and/or temperature data. A serial interface 124 can be provided to apprise the "outside world" of the condition of the battery.

Figure 9:
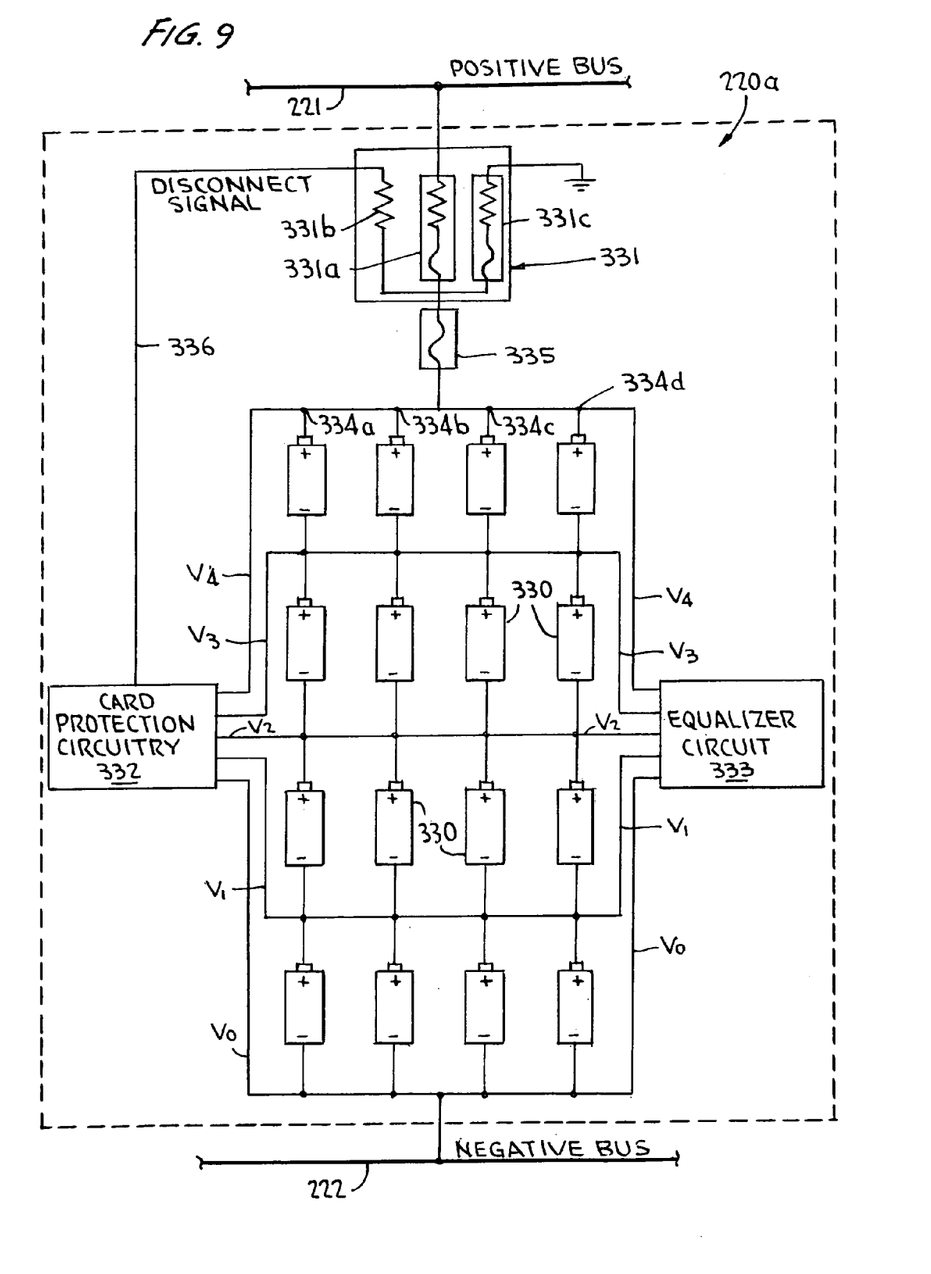
FIG. 9 is a block diagram of an exemplary cell card.

FIG. 9 illustrates schematically the circuit of an exemplary cell card 220a, that is, one embodiment of the cell cards 220a-n of FIG. 8. The FIG. 9 embodiment of the cell card 220a includes sixteen individual battery cells 330 connected in a series-parallel arrangement, such that there are four parallel connected arrays each of four series-connected cells 330. The invention is of course not thus limited. In accordance with FIGS. 1-4, the cells 330 are positioned in a space-efficient manner on a circuit card 10. Cell card protection circuitry 332 and equalizer circuits 333 can also reside on the respective cell card 10. As indicated herein, such circuitry 332, 333 can be located in the spacing created at the longitudinal intersection of cylindrical cells.

As shown in FIG. 9, the connection of the cell card 220 to the positive battery module power bus 221 can be controlled (e.g., interrupted) by a controllable cell card disconnect device 331 activated responsive to a signal from a cell card protection circuit 332. The cell card protection circuit 332 monitors the cells 330 of the cell card 220a to identify criteria indicative of cell failure; various criteria may be used based on the embodiment. Cell card protection device/circuitry 332 can include analog and/or digital hardware, and/or software. For example, in one embodiment, cell card protection circuitry 332 monitors cell voltage across each cell 330 (as indicated by parallel connection of the rows of series-connected cells) and activates the cell card disconnect device 331 when one or more of the battery cells 330 within cell card 220a have a terminal voltage that exceeds a predetermined value.

In the embodiment shown, the cell card 220a has four rows of cells 330. Each row contains four parallel cells. The four rows are connected in series to provide a total output voltage from the cell card that is the summation of the voltages of each of the four rows within the card. Again, in this embodiment, the cell card electronics is arranged to monitor and equalize the entire row as a unit (e.g., the entire row of four cells is treated as if it were a single cell). The positive connection to row 1 is designated as V1 in FIG. 9, the positive connection to row 2 as V2, and so forth. In the preferred microcontroller implementation, each positive row connection (V1 through V4) is brought to a voltage dividing resistor network (not shown) to reduce the row voltage to a level that is compatible with the microcontroller (preferably less than 3.3 Vdc). All row voltages are referenced to the negative connection of row 1 as designated by Vo in FIG. 9; Vo is thus the cell card negative reference, also referred to as cell card ground. The microcontroller (not shown, but connected across the rows of cells as is the equalizer circuit 333 in FIG. 9) has an internal multiplexer that sequentially samples each row voltage. The microcontroller performs a difference calculation, that is, subtracts the current row voltage sample from the previous row voltage sample. For example, if row 1 voltage (V1) is 4 volts relative to row 1 negative and the row 2 voltage (V2) is 8 volts relative to row 1 negative, then the microcontroller subtracts 8 volts from 4 volts to produce a differential row 2 voltage (V2−V1) of 4 volts. This is then compared to a reference value to determine whether there is a fault.

In addition to looking for cells that exceed a maximum reference voltage for activating the protection switch, the difference between the highest cell voltage and the lowest cell voltage in the card can be compared to a preset maximum value. If the diffence is greater than the maximum, the protection switch is activated, because very large deviations in cell voltages indicate a failed cell or failed card electronics. The comparison is preferably disabled when the highest cell voltage is below a preset value. This is to prevent a false activation of the protection switch at lower cell voltages, as there are inherently large deviations in cell voltage at low charge levels.

Other illustrative criteria to which the disconnect device may be responsive can be based on whether there is data and/or evidence of actual and/or potential battery cell damage within a cell card 220*a*, if continued operation of a cell card 220*a* may be detracting from the overall performance of the module, etc. As noted above, in some embodiments, the battery modules 101*a-n* of a given battery design will be designed to comprise a sufficient number of cell cards 220*a-n* such that battery performance will still be satisfactory when a single one of cell cards 220*a-n* is disconnected from the module power bus 221; this design is useful when it is particularly difficult to replace the battery module.

In one embodiment, illustrated in FIG. 9, the cell card disconnect device 331 can be configured as a controllable thermal cut-off (CTCO) device. The CTCO can be constructed using a conventional thermal cut-off (TCO) circuit element 331*a*, that is, a device the continuity of which is permanently destroyed by heat, provided, for example, by energizing a heating resistor 331*b* juxtaposed thereto. That is, the disconnect signal 336 received from the cell card protection device/circuitry 332 provides a current to resistor 331*b*, which heats TCO 331*a* and causes it to be opened permanently. Power to the heating resistor 331*b* is then terminated by a second TCO 331*c* in series with resistor 331*b* that can be set to a higher opening temperature than the first TCO 331*a* or is otherwise arranged so that it cuts off power to resistor 331*b* only after first TCO 331 is opened. In order that the components of the CTCO 331 can be in thermal contact with one another, they may assembled onto a thermally conductive pad or bonded to one another using a thermally-conductive potting compound.

The FIG. 9 embodiment also includes an equalizer circuit 333 that can balance the state-of-charge between the series-connected cells 330 within a cell card 220*a* for the purposes of better matching the charge and discharge characteristics of cells 330. One exemplary embodiment for a passive equalizer circuit 333, provided for each cell or row of cells, is shown in FIG. 10. In the embodiment shown, a comparator 441 senses when the voltage across cell 330 exceeds a predetermined voltage set-point, set by a reference voltage source 442. Reference source 442 comprises an integrated circuit which employs the summed voltage of the series-connected cells within the cell card (the connections to the cells not being shown in FIG. 10) to provide a tightly regulated comparison voltage. When the set-point presented by the reference source 442 is exceeded, a field effect transistor (FET) 443 is turned on to bypass charge current around the battery cell 330, and into a resistor 444 and/or another device, to be dissipated as heat. An identical circuit to that of FIG. 9 is attached to each series connected cell within the cell card. Only the equalizer circuits that are assigned to a cell that exceeds the voltage reference are activated to dissipate energy to the resistor. In this way, only the cells that are higher in charge are forced to dissipate some of their energy to the resistor. This allows cells that are lower in charge to accumulate energy at a higher rate, and "catch-up" to the cells that are higher in charge.

Accordingly, at least a portion of an overcharging cell's energy can be dissipated to avoid damage. Those of ordinary skill will recognize that the methods and systems are not limited by the equalizer device/circuit 333 and/or components thereof, and that other analog and/or digital designs can be employed to provide the equalization as provided herein.

In the currently preferred embodiment, equalizer circuit 333 contains four of the circuits of FIG. 10, one for each of the four rows of cells. At some cost in complexity, the same circuit could be provided for each cell, or the same circuit could be multiplexed row-by-row, or cell-by-cell. The analog circuit shown could also be replaced by a digital circuit, in which the reference and comparator ciruits are implemented digitally, while the transistor 443 and resistor 444 would typically still be provided as discrete components.

With further reference to FIG. 9, the arrangement of over-current and over-temperature protection within a cell card 220 depends on battery cell design and battery cell chemistry. For example, some small lithium-ion cells are factory-equipped with a resettable Polymeric Positive Temperature Coefficient (PPTC) fuse and/or an internal TCO that is not resettable. In such embodiments, the cell card protection circuitry 332 can be simplified. For example, in such a embodiment, cell card protection circuitry 332 can protect cells 330 from overcharge by activating the cell card disconnect device 331 when one or more cells 330 within a cell card 220*a* has a terminal voltage above a predetermined maximum value. Where the preferred battery cells 330 do not include internal protection devices, external cell protection devices (which might well also include PPTC fuses) can be located, e.g., at 334*a-d* (FIG. 9) although those of ordinary skill will understand that other locations may alternatively or additionally be used. At least one thermal cut-off (TCO) device can also be installed in a location likely to experience a relatively high temperature in the event of a failure, and used similarly to disconnect the cell or cell card, as appropriate.

The features of cell card protection circuitry 332 may be expanded when cells 330 do not include or otherwise contain factory-equipped protection devices. For example, in one embodiment, the cell card protection circuitry 332 can protect battery cells 330 when one or more of the cells 330 within a cell card 220*a* has a terminal voltage above a predetermined value, or if one or more points within a cell card 220*a* are above a predetermined temperature value. One or more positive temperature coefficient characteristic ("PPTC") devices can be used to protect cells 330 from over-current conditions and to balance current flow between parallel cell cards. When one cell card begins to support an unequal share of the battery module load current, the PPTC resistance will increase and limit the amount of current flowing from the cell card. When the short condition is removed, the PPTC device resets itself.

This circuitry can be implemented in "discrete hardware" and "microcontroller" versions. In the former, there is no multiplexing. Each cell has an independent equalizer circuit, and an independent sensing circuit, as in FIG. 10, to activate the protection circuit if there is a very high cell voltage. In the microcontroller version, the microcontroller, one of which is provided for each cell card, has an internal multiplexer that compares the voltage across each cell in succession to a reference value. When appropriate, the microcontroller activates the appropriate equalizer transistor (connected as transistor 443 in FIG. 10) to begin dissipating energy from cells that are high in charge. The microcontroller may also be capable of "burning open" the cell card protection switch (e.g., causing resistor 331*b* to open permanently-openable switch 331*a*), disconnecting the entire cell card, if a cell voltage exceeds another reference value, indicating that a cell is severely overcharging cell.

Referring again to FIG. 9, a cell card can include one or more electrical fuses 335 to increase the current interrupt rating of the PPTC devices, since the interrupt rating of PPTC devices within battery cells 330 or PPTC devices 334a-d in series with battery cells 330 may not sustain a short circuit current, as may occur if there is a hard short in a battery cell card 200a that is fed by the other parallel cell cards in the module. More specifically, PPTC devices do not burn-out instantaneously, so there is a finite time where they must sustain a very high short circuit current while they are beginning to open up. The peak value of this current is referred to as the interrupt rating. It is usually much higher than the basic PPTC device rating. If the interrupt rating is insufficient, the case of the PPTC device may explode in the process of opening. The protection from the fuse 335 can be evaluated relative to possible permanent loss in battery module output due to an opening of fuse 335 during a momentary short circuit across one or more of modules 101a-d. In some battery powered systems, it may be desirable to risk the venting or even rupturing of one of the small cells rather than risk losing power from the entire battery pack. That is, if the entire pack is shorted, fuses 335 (if provided) may open permanently on a number of cell cards in a very short time period. By comparison, because the PPTC devices have the ability to reset themselves after the shorting condition is removed, the interruption will be temporary. Accordingly, it may be preferable to eliminate fuse 335 and risk the possibility of exploding a PPTC device due to insufficient interrupt rating rather than permanently disabling the battery pack.

To summarize the advantages of the invention, referring back to FIG. 7, the provision of protection circuitry 105a-n for each module enables the connection of multiple battery modules 101a-n in series, and further, a convenient and readily manufacturable physical arrangement as shown in FIGS. 2-6 herein. Module protection circuitry controls the interlock signal 106 to open pack disconnect device 102 and interrupt the connection of battery pack to the charger 104 and/or load 103. In a typical embodiment, the module interlock signal 106 can be responsive to a failure due to module over-voltage, module under-voltage, and/or module over-temperature.

Thus, according to the invention, a large battery pack of specified voltage and capacity can be assembled from a plurality of identical small cells by the following steps. The required battery capacity is first divided by the nominal module capacity, to determine the number of modules, and the module capacity is divided by the cell card capacity, to determine the total number of parallel cell cards within a module. The number of cells per cell card, and their series/parallel connection, is determined similarly. The cell cards are then connected in parallel to a common power bus to form a battery module. A plurality of battery modules then can be connected in series to produce the required pack voltage.

As indicated above, the advantages of the modular structure of a battery module according to the invention include the following: A manufacturer can design and have made up in advance a number of different sizes of cell cards, that is, designed to accommodate different numbers of cells. Then, in order to manufacture a battery pack of desired dimensions and capability, the appropriate module sizes are chosen, and the cells assembled into cell cards and the cell cards into modules accordingly. Assembly of the cylindrical cells on identical cell cards made of flameproof circuit-board material disposed parallel to one another provides numerous advantages. Because the cards are parallel to one another and flameproof, the risk of fire spreading from one cell or group of cells to another is reduced. Because the cells are typically cylindrical and secured to planar cards, convenient spaces are provided for protection and interconnection circuitry, and integral ventilation ducts for cooling air are formed therebetween. Because the cell cards are identical and have the connections brought out to the edges, the connection between the cell cards can be made by readily-manufactured, solid bus bars, thus providing an efficient way making the electrical connections which simultaneously strengthens the mechanical assembly. Further, the cell card circuit boards act as a mechanical barrier, resisting the ability of a sharp object from protruding deep into the battery module.

Although the methods and systems of the invention and the batteries produced thereby have been described relative to a specific embodiment thereof, they are not so limited. Obviously, many modifications and variations may become apparent in light of the above teachings. For example, a battery call card stack 35 according to FIG. 3 may be used without the enclosure 55 of FIG. 5, or more than one cell card stack may be fitted into a single enclosure 55 to add to the capacity or voltage of the battery module. Internal busses 30a, 30b may be attached to various other locations on the cell cards. The cell cards 1 can be sized to accommodate a larger or smaller number of cells, and/or can be designed and/or sized to accommodate other cell geometries besides cylindrical types Many additional changes in the details, materials, and arrangement of parts, herein described and illustrated, can be made by those skilled in the art. Accordingly, it will be understood that the disclosed methods and systems are not to be limited to the embodiments disclosed herein, can include practices otherwise than specifically described, and are to be interpreted as broadly as allowed under the law.

What is claimed is:

1. A method for assembling a battery pack of specified capacity from a plurality of cells assembled to planar circuit boards in order to comprise at least two substantially identical planar cell cards, comprising the steps of:

dividing the specified capacity by a nominal battery module capacity, to determine a desired number of parallel modules to be provided, dividing the nominal battery module capacity by a nominal cell card capacity, to determine the number of cell cards required in each module, dividing the nominal cell card capacity by the cell capacity, to determine the number of cells to be provided in each cell card, providing a number of planar circuit boards of fire-resistant material equal to the required number of cell cards, assembling the cells to the planar circuit boards so as to provide the planar cell cards, said cells being generally elongated cylindrical members, having terminals at their opposed ends, and being arranged on said cell cards and connected end-to-end to form at least two series-connected linear arrays on each card, said arrays being disposed physically parallel to one another on each card so as to define at least two rows of side-by-side cells, with the axes of said cylindrical cells parallel to the plane of said planar circuit boards, assembling the at least two substantially identical cell cards to comprise the desired number of cells in a suitable series/parallel circuit, each cell card having positive and negative terminals, by arranging the planar cell cards parallel to one another, and connecting the at least two cell cards in parallel by connecting elongated bus bars to the positive and negative terminals of each card so as to comprise the battery module(s), whereby the bus bars extend orthogonally to the parallel planar cell cards and make electrical and mechanical connection between the cell cards, and whereby passages for ventilating air and/or hot gases resulting from damage to one or more cells are formed between the cylindrical cells and the planar cell cards, each said cell card comprising cell monitoring circuitry for monitoring the condition of the cells on the cell card, and for disconnecting the cell card from the elongated bus bars in response to detection of a fault, connecting the modules(s) in parallel to obtain the specified battery pack capacity and in series to obtain the specified battery pack voltage, and disposing the assembled modules in a closely-fitting enclosure so that the cell cards effectively subdivide the interior of the enclosure, limiting the spread of fire within the enclosure; and wherein the cell cards are notched at their ends to cooperate with said enclosure so as to define ducts extending transverse to said cell cards in communication with said passages between said cylindrical cells and said cell cards for ventilating air and/or hot gases.

2. The method of claim 1, further comprising the step of connecting said cell monitoring circuitry in parallel across each row of cells, for monitoring the condition of the cells in each row.

3. A battery pack made up of a number of generally cylindrical elongated cells having terminals at opposed ends thereof, the cells being organized in series/parallel format and assembled to at least two planar circuit boards of fire-resistant material so as to make up a like number of substantially identical cell cards of desired capacity, each said cell card comprising cell monitoring circuitry for monitoring the condition of the cells on the cell card, and for disconnecting the cell card from the elongated bus bars in response to detection of a fault, each cell card comprising at least four cells, the at least four cells on each card being arranged in at least two linear arrays of least two serially-connected cells, said arrays being disposed physically parallel to one another, such that the cells of the at least two arrays form at least two rows, the axes of the cylindrical cells being disposed parallel to the plane of the corresponding planar circuit boards, the cell cards being organized in parallel to form modules of desired capacity, the modules being connected in series and parallel to form the battery pack, and wherein the substantially identical cell cards have positive and negative electrical terminals on their edges, are arranged parallel to one another, and are connected mechanically and electrically by elongated bus bars extending orthogonally to said cell cards and connected to said positive and negative terminals on each cell card, such that passages for ventilating air and/or hot gas are defined between the cell cards and cells, the assembly of cell cards being disposed within an enclosure, such that the cell cards subdivide the interior of the enclosure so as to limit the spread of fire, and wherein the cell cards are formed so as to cooperate with the enclosure to define ducts extending transversely to said planar circuit boards for the passage of ventilating air and/or hot gas in communication with said passages formed between the cells and cell cards.

4. The battery pack of claim 3, wherein said cell monitoring circuitry is connected in parallel across the cells of each row.

* * * * *